United States Patent
Ohno

(10) Patent No.: US 11,647,263 B2
(45) Date of Patent: May 9, 2023

(54) CAMERA HEAD AND ENDOSCOPE

(71) Applicant: Sony Olympus Medical Solutions Inc., Tokyo (JP)

(72) Inventor: Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/533,145

(22) Filed: Nov. 23, 2021

(65) Prior Publication Data

US 2022/0086310 A1 Mar. 17, 2022

Related U.S. Application Data

(63) Continuation of application No. 16/236,784, filed on Dec. 31, 2018, now abandoned.

(30) Foreign Application Priority Data

Feb. 28, 2018 (JP) .............................. JP2018-035809

(51) Int. Cl.
*H04N 5/225* (2006.01)
*A61B 1/04* (2006.01)
(Continued)

(52) U.S. Cl.
CPC ....... *H04N 5/2251* (2013.01); *A61B 1/00006* (2013.01); *A61B 1/00066* (2013.01);
(Continued)

(58) Field of Classification Search
CPC .......... H04N 5/2251; H04N 2005/2255; A61B 1/00006; A61B 1/00066; A61B 1/00105;
(Continued)

(56) References Cited

U.S. PATENT DOCUMENTS 4,323,304 A * 4/1982 Ishii .................... G02B 23/2484
396/17
4,697,894 A * 10/1987 Takamura .......... A61B 1/00128
359/503
(Continued)

FOREIGN PATENT DOCUMENTS

JP H06214168 A 8/1994
JP 2015-134039 A 7/2015

*Primary Examiner* — Amir Shahnami
*Assistant Examiner* — Matthew David Kim
(74) *Attorney, Agent, or Firm* — Xsensus LLP

(57) ABSTRACT

A camera head includes a mounting unit detachably connected to an eyepiece unit of an endoscope, the camera head capturing an object image emitted from the eyepiece unit. The eyepiece unit includes an abutting surface that is orthogonal to a central axis along an insertion direction of the endoscope into a subject, and the abutting surface extending over an entire circumference in a circumferential direction around the central axis. The mounting unit is connected to the eyepiece unit and is configured to relatively rotate the endoscope and the camera head around the central axis. The mounting unit includes a facing surface that faces the abutting surface, and a pressing portion that abuts the eyepiece unit and presses the eyepiece unit toward the facing
(Continued)

surface along the central axis. The facing surface includes a projecting portion that projects toward the abutting surface and abuts the abutting surface.

20 Claims, 12 Drawing Sheets

(51) Int. Cl.
*A61B 1/00* (2006.01)
*A61B 1/045* (2006.01)
*A61B 1/07* (2006.01)
*A61B 1/06* (2006.01)

(52) U.S. Cl.
CPC ...... *A61B 1/00105* (2013.01); *A61B 1/00126* (2013.01); *A61B 1/00128* (2013.01); *A61B 1/00195* (2013.01); *A61B 1/042* (2013.01); *A61B 1/045* (2013.01); *A61B 1/0669* (2013.01); *A61B 1/07* (2013.01); *H04N 2005/2255* (2013.01)

(58) Field of Classification Search
CPC ............ A61B 1/00126; A61B 1/00128; A61B 1/00195; A61B 1/042; A61B 1/045; A61B 1/0669; A61B 1/07
USPC .......................................................... 348/73
See application file for complete search history.

(56) References Cited

U.S. PATENT DOCUMENTS

| | | |
|---|---|---|
| 5,792,045 A | 8/1998 | Adair |
| 6,080,101 A | 6/2000 | Tatsuno |
| 2001/0049313 A1* | 12/2001 | Rutz ..................... B62D 55/08 474/202 |
| 2005/0272976 A1* | 12/2005 | Tanaka ................ A61B 1/0016 600/114 |
| 2006/0229495 A1* | 10/2006 | Frith .................. A61B 1/00126 600/112 |
| 2010/0230223 A1* | 9/2010 | Wu ........................ A45C 5/143 190/18 A |
| 2014/0094657 A1 | 4/2014 | Miyamoto et al. |
| 2016/0169433 A1 | 6/2016 | Askestad |

\* cited by examiner

CAMERA HEAD AND ENDOSCOPE

CROSS-REFERENCE TO RELATED APPLICATIONS

This application is a continuation of U.S. application Ser. No. 16/236,784, filed Dec. 31, 2018, which claims priority to and incorporates by reference the entire contents of Japanese Patent Application No. 2018-035809 filed in Japan on Feb. 28, 2018.

BACKGROUND

The present disclosure relates to a camera head and an endoscope.

In the medical field or the industrial field, there is known an endoscope apparatus for observing an inside of a subject such as a human or a mechanical structure (for example, see JP 2015-134039 A).

The endoscope apparatus described in JP 2015-134039 A includes an endoscope, which imports an object image of the inside of the subject so as to emit the image from an eyepiece unit, and a camera head, which has a mounting unit (coupler unit) that is detachably connected to the eyepiece unit and captures the object image emitted from the eyepiece unit.

Further, the mounting unit is provided with a mounting recessed portion into which the eyepiece unit is inserted. Further, in a state in which the eyepiece unit is inserted into the mounting recessed portion, and the eyepiece unit is mounted on the mounting unit, the endoscope and the camera head come into a state of being relatively rotatable around a central axis of the endoscope in an insertion direction into the subject.

SUMMARY

Incidentally, a bottom surface of a mounting recessed portion is configured of a flat surface orthogonal to a central axis of an endoscope, in general. On the other hand, an end surface of an eyepiece unit on a proximal end side (side separated from a distal end of the endoscope) is also configured of a flat surface orthogonal to the central axis of the endoscope. In this manner, in a state in which the eyepiece unit is mounted on the mounting unit, the end surface of the eyepiece unit on the proximal end side and the bottom surface of the mounting recessed portion come into a state of abutting each other. In other words, a relatively large contact area is formed between the eyepiece unit and the mounting unit.

Hence, in a configuration in the related art, when an endoscope and a camera head are caused to relatively rotate around a central axis of the endoscope, a problem arises in that relatively high friction resistance occurs due to the relatively large contact area, and thus operability is likely to be degraded.

According to one aspect of the present disclosure, there is provided a camera head including a mounting unit which is detachably connected to an eyepiece unit of an endoscope, the camera head capturing an object image emitted from the eyepiece unit, wherein the eyepiece unit includes an abutting surface that is orthogonal to a central axis of the endoscope, the central axis being along an insertion direction of the endoscope into a subject, and the abutting surface extending over an entire circumference in a circumferential direction around the central axis, the mounting unit is connected to the eyepiece unit and is configured to relatively rotate the endoscope and the camera head around the central axis, the mounting unit includes a facing surface that faces the abutting surface, and a pressing portion that abuts the eyepiece unit and presses the eyepiece unit toward the facing surface along the central axis, and the facing surface includes a projecting portion that projects toward the abutting surface and abuts the abutting surface.

DETAILED DESCRIPTION

Figure 1:
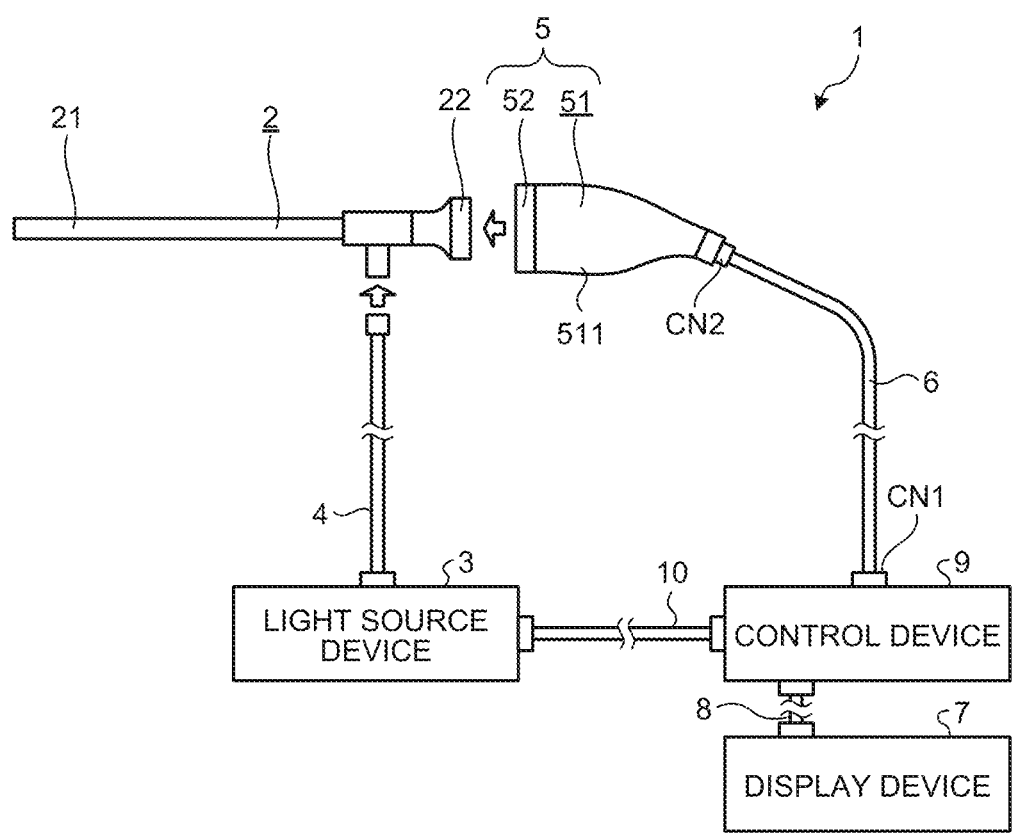
FIG. 1 is a diagram illustrating a schematic configuration of an endoscope apparatus according to a first embodiment.

Hereinafter, modes for carrying out the disclosure (hereinafter, embodiments) will be described with reference to the drawings. Incidentally, the disclosure is not limited to the embodiments to be described below. Further, the same reference signs are assigned to the same portions in the drawings.

First Embodiment

Schematic Configuration of Endoscope Apparatus

FIG. 1 is a diagram illustrating a schematic configuration of an endoscope apparatus 1 according to a first embodiment.

The endoscope apparatus 1 is used in the medical field and an apparatus for observing an inside of a living body. As illustrated in FIG. 1, the endoscope apparatus 1 includes an endoscope 2, a light source device 3, a light guide 4, a camera head 5, a first transmission cable 6, a display device 7, a second transmission cable 8, a control device 9, and a third transmission cable 10.

The endoscope 2 is configured of a rigid endoscope. In other words, the endoscope 2 has an elongated shape, of which the entire endoscope is rigid or a part thereof is flexible and the rest thereof is rigid, and is inserted into a living body. As illustrated in FIG. 1, the endoscope 2 includes an insertion unit 21 and an eyepiece unit 22.

The insertion unit 21 is a part that extends in a linear shape and is inserted into the living body. Inside the insertion unit 21, a configuration of one or a plurality of lenses is employed, and an optical system (not illustrated) that collects an object image is provided.

The eyepiece unit 22 is provided at a proximal end (right end portion in FIG. 1) of the insertion unit 21. Inside the eyepiece unit 22, an eyepiece optical system (not illustrated) that emits the object image collected by the optical system (not illustrated) inside the insertion unit 21 from the eyepiece unit 22 to the outside is provided.

Incidentally, a shape of the eyepiece unit 22 will be described below in detail.

The light source device 3 is connected to one end of the light guide 4 and supplies light for illuminating the inside of the living body to the end of the light guide 4 under control by the control device 9.

One end of the light guide 4 is detachably connected to the light source device 3, and the other end thereof is detachably connected to the endoscope 2. In this manner, the light guide 4 transmits the light supplied from the light source device 3 from one end to the other end and supplies the light to the endoscope 2. The light supplied to the endoscope 2 is emitted from a distal end (left end portion in FIG. 1) of the endoscope 2 and is radiated to the inside of the living body. The light that is radiated to the inside of the living body and is reflected from the inside of the living body (object image) is collected by the optical system (not illustrated) in the insertion unit 21.

The camera head 5 includes an airtight unit 51 (FIG. 1), inside which an image sensor (not illustrated) or the like is housed in an airtight manner, and a mounting unit 52 that is provided in the airtight unit 51 and is detachably connected to the eyepiece unit 22 of the endoscope 2. In this manner, the camera head 5 captures the object image collected in the endoscope 2 and outputs an image signal (RAW signal) generated by the corresponding capturing, under control by the control device 9. For example, the image signal is an image signal having 4K or more pixels.

Incidentally, a shape of the mounting unit 52 will be described below in detail.

One end of the first transmission cable 6 is detachably connected to the control device 9 via a connector CN1 (FIG. 1), and the other end thereof is detachably connected to the camera head 5 via a connector CN2 (FIG. 1). In this manner, the first transmission cable 6 is for transmitting the image signal or the like that is output from the camera head 5 to the control device 9 and transmitting each of a control signal, a synchronization signal, clock, electric power, and the like, which are output from the control device 9, to the camera head 5.

Incidentally, the image signal or the like from the camera head 5 to the control device 9 via the first transmission cable 6 may be transmitted as a light signal of the image signal or the like or may be transmitted as an electrical signal. The same is true of the transmission of the control signal, the synchronization signal, and the clock from the control device 9 to the camera head 5 via the first transmission cable 6.

The display device 7 is configured of using a liquid crystal display, an organic electro luminescence (EL) display, or the like, and displays a captured image based on a video signal from the control device 9, under control by the control device 9.

One end of the second transmission cable 8 is detachably connected to the display device 7, and the other end thereof is detachably connected to the control device 9. In this manner, the second transmission cable 8 is for transmitting the video signal processed by the control device 9 to the display device 7.

The control device 9 is configured to include a central processing unit (CPU) or the like and collectively controls operations of the light source device 3, the camera head 5, and the display device 7.

For example, the control device 9 executes various processes on the image signal acquired from the camera head 5 via the first transmission cable 6, thereby, thereby generating the video signal and outputting the video signal to the display device 7 via the second transmission cable 8. In this manner, the display device 7 displays a captured image based on the video signal. In addition, the control device 9 outputs the control signal or the like to the camera head 5 or the light source device 3 via the first or third transmission cable 6 or 10.

One end of the third transmission cable 10 is detachably connected to the light source device 3, and the other end thereof is detachably connected to the control device 9. In this manner, the third transmission cable 10 is for transmitting a control signal from the control device 9 to the light source device 3.

Configuration of Eyepiece Unit

Next, a configuration of the eyepiece unit 22 will be described.

Figure 2:
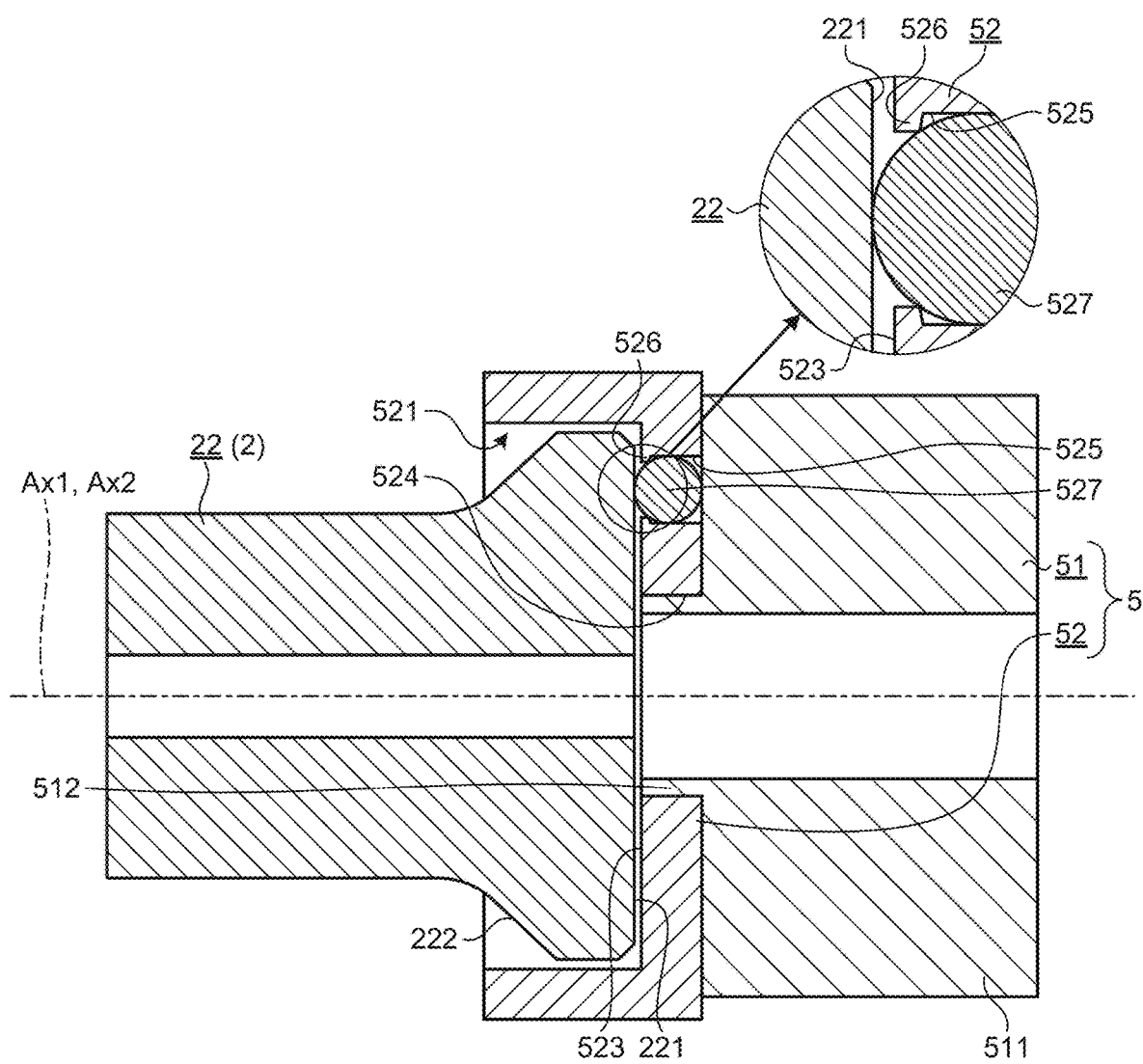
FIG. 2 is a sectional view illustrating a connecting part between an endoscope and a camera head.

FIG. 2 is a sectional view illustrating a connecting part between the endoscope 2 and the camera head 5. Specifically, FIG. 2 is a sectional view obtained by cutting the connecting part between the endoscope 2 and the camera head 5 on a cut plane including a central axis Ax1 of the endoscope 2 in an insertion direction into a subject. Incidentally, in FIG. 2, for convenience of description, the optical system that is provided in the endoscope 2, the image sensor that is provided in the camera head 5, and the like are omitted.

The eyepiece unit 22 has a substantially cylindrical shape.

An end surface of the eyepiece unit 22 on a proximal end side (a side of a right end portion in FIG. 2) is orthogonal to the central axis Ax1, extends over the entire circumference in a circumferential direction around the central axis Ax1, and functions as an abutting surface 221 (FIG. 2) according to the disclosure.

In addition, a distal end side (left side in FIG. 2) of an outer circumferential surface of the eyepiece unit 22 has a tapered shape that decreases in diameter toward the distal end side. In other words, the outer circumferential surface on the distal end side is separated from the central axis Ax1 toward the abutting surface 221 and functions as an inclined surface 222 (FIG. 2) according to the disclosure.

Configuration of Mounting Unit

Next, a configuration of the mounting unit 52 will be described with reference to FIGS. 2 and 3.

Figure 3:
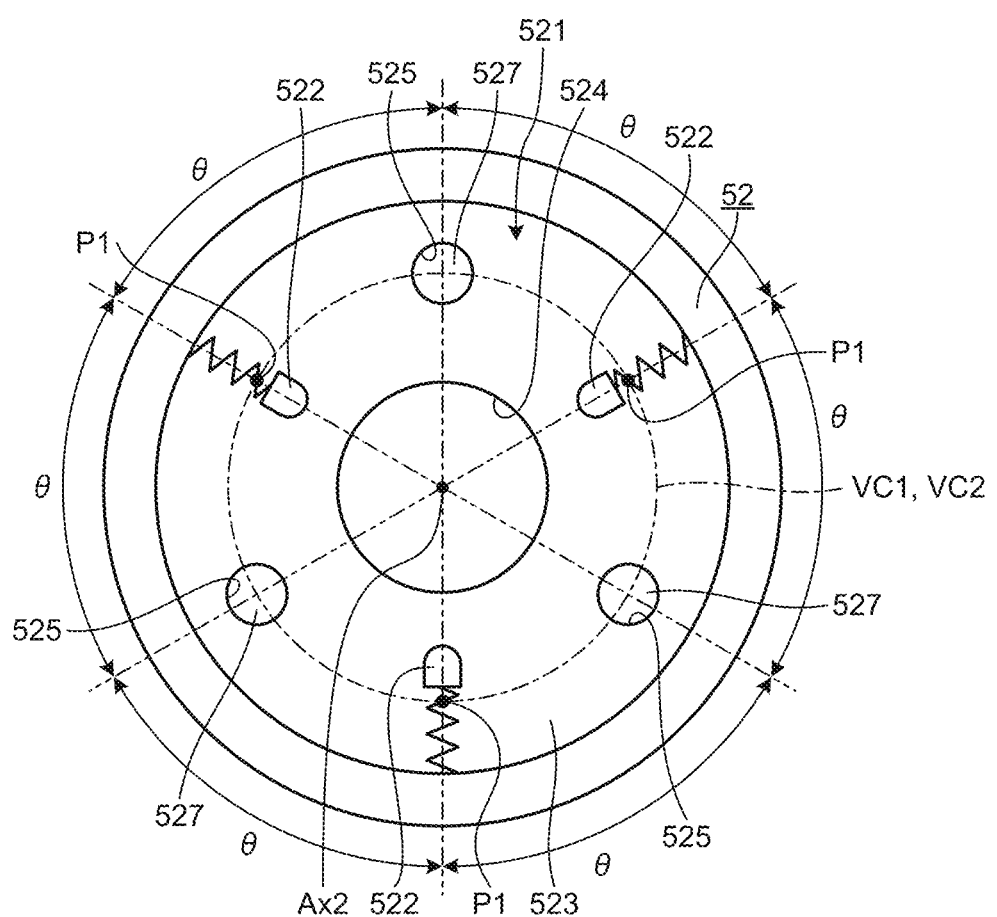
FIG. 3 is a view of a mounting unit viewed from a side on which an eyepiece unit is mounted.

FIG. 3 is a view of the mounting unit 52 viewed from a side on which the eyepiece unit 22 is mounted.

The mounting unit 52 has a substantially cylindrical shape.

As illustrated in FIG. 2 or 3, an end surface of the mounting unit 52 on the distal end side (side of a left end portion in FIG. 2) is provided with a mounting recessed portion 521 which is recessed toward the proximal end side (side of the right end portion in FIG. 2) and into which the eyepiece unit 22 is inserted. In this manner, in a state in which the eyepiece unit 22 is inserted into the mounting recessed portion 521, and the eyepiece unit 22 is mounted on the mounting unit 52, the central axis Ax1 matches a central axis Ax2 (FIGS. 2 and 3) of the mounting unit 52.

In addition, an inner circumferential surface of the mounting recessed portion 521 is provided with a pressing portion 522 (FIG. 3). Incidentally, the pressing portion 522 is omitted in FIG. 2, for convenience of description.

As illustrated in FIG. 3, three pressing portions 522 are provided and have the same shape as each other. In addition, the pressing portions 522 are each provided at rotationally symmetrical positions at intervals of 120° around the central axis Ax2. In this manner, the pressing portion 522 has elasticity to be movable in an approaching/separating direction to and from the central axis Ax2, abuts the inclined surface 222, and presses the eyepiece unit 22 toward a bottom part of the mounting recessed portion 521 along the central axis Ax2.

In this manner, the endoscope 2 and the camera head 5 are configured to be relatively rotatable around the central axis Ax1 (Ax2) in a state of being connected to each other.

In addition, the recessed portion of the mounting recessed portion 521 faces the abutting surface 221 and functions as a facing surface 523 (FIGS. 2 and 3) according to the disclosure.

In this manner, as illustrated in FIG. 2 or 3, the mounting unit 52 is provided with a communication hole 524 and an attachment hole 525 that penetrate the mounting unit from the end surface thereof on the proximal end side to the facing surface 523.

The communication hole 524 is configured of a circular hole having the center that matches the central axis Ax2. A part of the airtight unit 51 on the distal end side (side of a left end portion in FIG. 2) is connected to the communication hole 524.

Here, as illustrated in FIG. 2, a casing 511 that configures the airtight unit 51 is provided with a connection portion 512 that is positioned on the central axis Ax2 and projects from the distal end side (side of a left end portion in FIG. 2) of the casing 511. The connection portion 512 is formed to have a cylindrical shape having an outer diameter dimension that is substantially equal to an inner diameter dimension of the communication hole 524. In this manner, the connection portion 512 is inserted into the communication hole 524, and thereby the mounting unit 52 is connected to the airtight unit 51. Incidentally, an opening of the connection portion 512 is sealed by an optical element (not illustrated) in an airtight manner.

The attachment hole 525 is configured of a circular hole. As illustrated in FIG. 3, three attachment holes 525 (the same number of pressing portions 522) are provided and have the same shape as each other. In addition, the attachment holes 525 are each provided at rotationally symmetrical positions at intervals of 120° around the central axis Ax2 on a first virtual circle VC1 around the central axis Ax2. Here, on the distal end side (side of a left end portion in FIG. 2) of the inner circumferential surface of the attachment hole 525, a drop preventing protrusion 526 projecting toward the inside of the attachment hole 525 is provided. In this manner, as illustrated in FIG. 2 or 3, a projecting portion 527 is housed inside the attachment hole 525.

Three projecting portions 527 are each configured of a ball (spherical body) having an outer diameter dimension that is substantially equal to an inner diameter dimension of the attachment hole 525. In this manner, the projecting portion 527 is housed in the attachment hole 525 from a proximal end side (side of a right end portion in FIG. 2), the proximal end side of the attachment hole 525 is blocked by the casing 511, and thereby the projecting portion is attached to the mounting unit 52. In this state, the projecting portions 527 come into a state in which a part of each of the projecting portions projects from the facing surface 523 toward the abutting surface 221 and is rotatably attached to the mounting unit 52. In addition, in a state in which the eyepiece unit 22 is mounted on the mounting unit 52, the projecting portion 527 abuts the abutting surface 221. In other words, the projecting portion 527 has a curved surface having an arc shape in cross-sectional view and abuts the abutting surface 221 by the curved surface.

Positional Relationship between Convex portion and Pressing Position by Pressing Portion Next, a positional relationship between the projecting portion 527 and a pressing position by the pressing portion 522 will be described with reference to FIG. 3.

Incidentally, a point P1 illustrated in FIG. 3 represents a position at which the pressing portion 522 abuts the inclined surface 222. Hereinafter, the point P1 is described as a pressing position P1. As described above, the pressing portion 522 has elasticity to be movable in the approaching/separating direction along the central axis Ax2. Therefore, in FIG. 3, the pressing position P1 is illustrated at a position separated from the central axis Ax2 from a "position of the pressing portion 522 in a free state in which the pressing portion is yet to abut the inclined surface 222" in FIG. 3.

As illustrated in FIG. 3, the three pressing positions P1 are positioned on a second virtual circle VC2 around the central axis Ax2. In this manner, the second virtual circle VC2 matches the first virtual circle VC1 on which projecting ends of the three projecting portions 527 are positioned, when viewed from a direction along the central axis Ax2. In addition, the three pressing positions P1 are positioned at positions deviated by 60° in the rotation direction around the central axis Ax2 with respect to the three projecting portions 527. In other words, each of the pressing positions P1 is positioned at a position at which angles θ in the rotation direction to the adjacent projecting portions 527 in the rotation direction are all the same angle of 60°.

The first embodiment described above has the following effects.

In the camera head 5 according to the first embodiment, the facing surface 523 is provided with the projecting portions 527 that project toward the abutting surface 221 and abut the abutting surface 221. In other words, the relatively small contact area is formed between the eyepiece unit 22 and the mounting unit 52 due to the projecting portions 527.

Hence, in the camera head 5 according to the first embodiment, when the endoscope 2 and the camera head 5 are caused to relatively rotate around the central axis Ax1 (Ax2), an effect is achieved in that relatively low friction resistance occurs due to the relatively small contact area, and thus it is possible to improve operability.

Incidentally, a constant clearance is set between the inner circumferential surface of the mounting recessed portion 521 and the outer circumferential surface of the eyepiece unit 22, with consideration for insertability of the eyepiece unit 22 into the mounting recessed portion 521. In other words, in a state in which a part of the outer circumferential surface of the eyepiece unit 22 abuts a part of the inner circumferential surface of the mounting recessed portion 521, the central axis Ax1 and the central axis Ax2 come into a state of being deviated from each other. In this state, a captured image acquired when an object image imported to the endoscope 2 is captured by the camera head 5 is likely to show a state in which a part of a circumferential edge side deviated from a center in the object image is blurred. In particular, in a case where an image sensor having 4K or more pixels is used as the image sensor provided in the camera head 5, the blurring state is remarkable.

In the camera head 5 according to the first embodiment, the pressing portions 522 are each provided at the rotationally symmetrical positions at intervals of 120° around the central axis Ax2 on the second virtual circle VC2 around the central axis Ax2. Therefore, the three pressing portions 522 press the inclined surface 222, and thereby, it is possible to cancel the deviation between the central axes Ax1 and Ax2 such that it is possible to position the eyepiece unit 22 at a position at which the central axes Ax1 and Ax2 match each other. In other words, the captured image does not show the state in which a part of the circumferential edge side of the object image is blurred.

In particular, in a case where a relatively large contact area is formed between the eyepiece unit 22 and the mounting unit 52 as described in the configuration in the related art, it is not possible to cancel the deviation between the central axes Ax1 and Ax2 even with a pressing force by the pressing portion 522, in some cases. In the camera head 5 according to the first embodiment, the relatively small contact area is formed as described above, and thus it is possible to easily cancel the deviation between the central axes Ax1 and Ax2 with the pressing force by the pressing portion 522.

In addition, in the camera head 5 according to the first embodiment, the projecting portions 527 are configured of balls (spherical bodies). Therefore, when the endoscope 2 and the camera head 5 are caused to relatively rotate around the central axis Ax1 (Ax2), the projecting portions 527 rotationally move on the abutting surface 221. In other words, it is possible to significantly reduce the friction resistance, and it is possible to further improve the operability.

In addition, in the camera head 5 according to the first embodiment, the projecting portions 527 and the pressing positions P1 by the pressing portions 522 are each provided at the rotationally symmetrical positions at intervals of 120° around the central axis Ax2 on the first and second virtual circles VC1 and VC2 which match each other, when viewed in the direction along the central axis Ax2. In addition, the three pressing positions P1 are positioned at positions deviated by 60° in the rotation direction around the central axis Ax2 with respect to the three projecting portions 527. Therefore, it is possible to apply the pressing force uniformly to the eyepiece unit 22 from the three pressing portions 522, and it is possible to support (abut) the eyepiece unit 22 uniformly by the three projecting portions 527. In other words, it is possible to smoothly position the endoscope 2 with respect to the camera head 5 in all of the directions of the direction along the central axis Ax1 (Ax2), the direction orthogonal to the central axis Ax1 (Ax2), and the rotation direction around two axes orthogonal to the central axis Ax1 (Ax2).

Second Embodiment

Next, a second embodiment will be described.

In the following description, the same reference signs are assigned to the same configurations as those in the first embodiment described above, and thus detailed description thereof is omitted or simplified.

Figure 4:
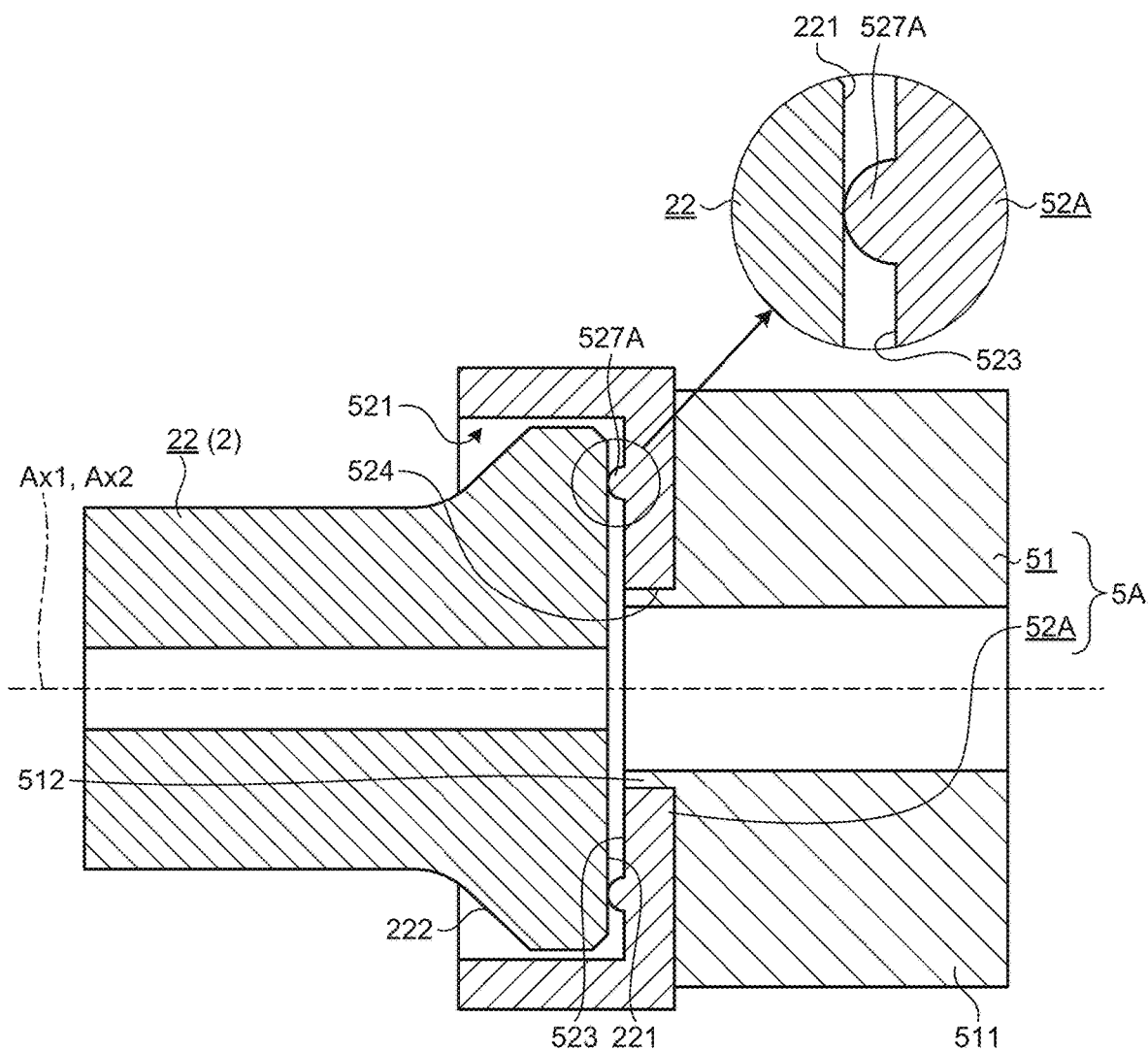
FIG. 4 is a view illustrating a configuration of a mounting unit according to a second embodiment.
Figure 5:
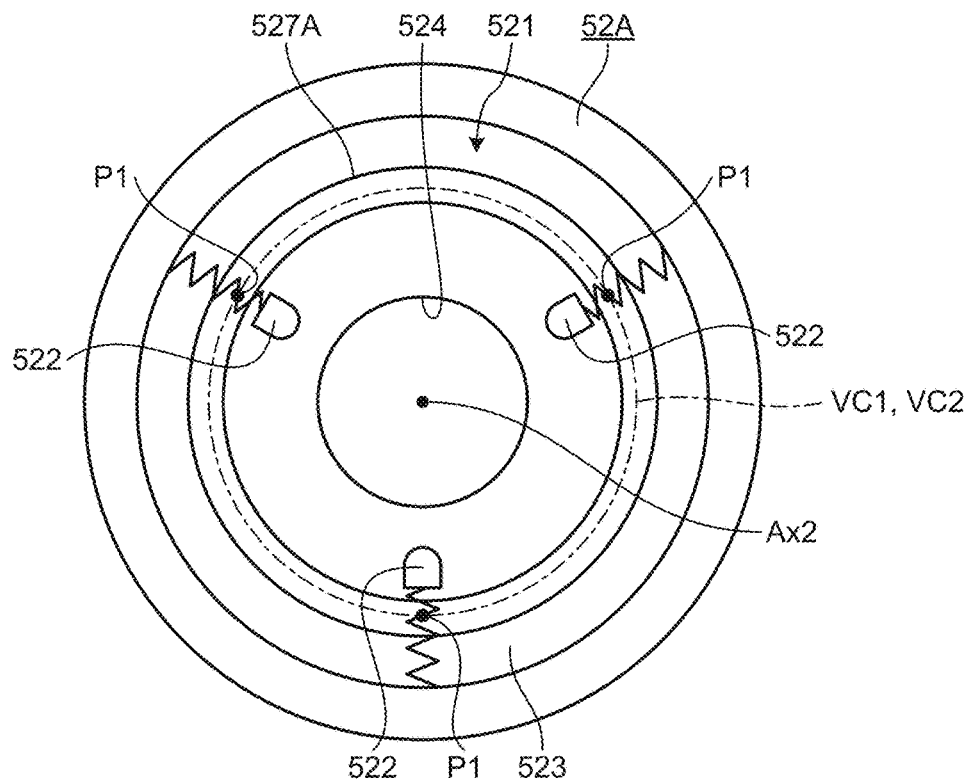
FIG. 5 is a view of the mounting unit viewed from a side on which an eyepiece unit is mounted.

FIG. 4 is a cross-sectional view corresponding to FIG. 2, the view illustrating a configuration of a mounting unit 52A according to the second embodiment. FIG. 5 is a view of the mounting unit 52A viewed from a side on which the eyepiece unit 22 is mounted.

In a camera head 5A (mounting unit 52A) according to the second embodiment, as illustrated in FIG. 4 or 5, there is employed a projecting portion 527A having a different configuration from that of the projecting portion 527 in the camera head 5 (mounting unit 52) described in the first embodiment described above.

Incidentally, in the mounting unit 52A according to the second embodiment, the projecting portion 527A having the different configuration from that of the projecting portions 527 is employed, and thus the attachment hole 525 (including drop preventing protrusion 526) is not provided.

As illustrated in FIG. 4 or 5, the projecting portion 527A is integrally formed on the facing surface 523. The projecting portion 527A projects toward the abutting surface 221 and has an annular shape extending over the entire circumference in the circumferential direction around the central axis Ax2. In addition, in a case of being cut by a plane including the axis Ax2, as illustrated in FIG. 4, the projecting portion 527A has a semi-circular shape in the cross-sectional view (arc shape). In this manner, in a state in which the eyepiece unit 22 is mounted on the mounting unit 52A, the projecting portion 527A abuts the abutting surface 221 by the curved surface having the semi-circular shape in the cross-sectional view.

Incidentally, a projecting end of the projecting portion 527A configures the first virtual circle VC1 described in the first embodiment described above and matches the second virtual circle VC2, when viewed from the direction along the central axis Ax2.

Even in a case of employing the projecting portion 527A as described in the second embodiment described above, the same effects as those of the first embodiment are achieved.

Modification Example of Second Embodiment

Figure 6:
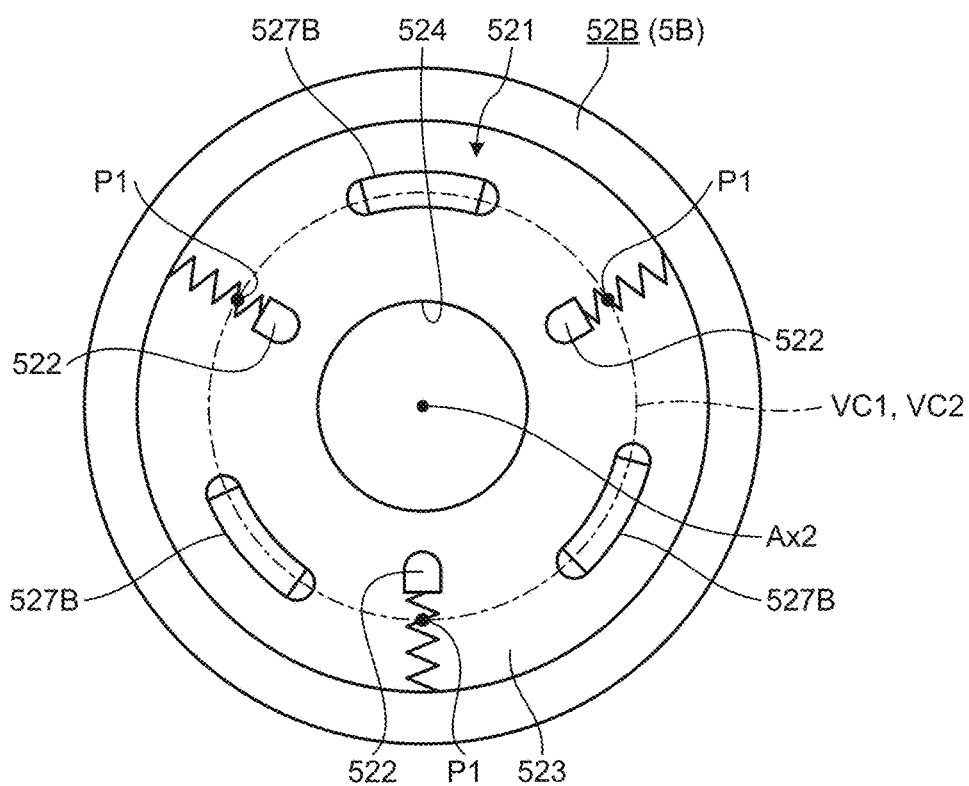
FIG. 6 is a view illustrating a modification example of the second embodiment.

FIG. 6 is a view corresponding to FIG. 5, the view illustrating a modification example of the second embodiment.

In the second embodiment described above, the projecting portion 527A has the annular shape extending over the entire circumference in the circumferential direction around the central axis Ax2; however, the shape of the projecting portion is not limited thereto.

For example, as illustrated in a camera head 5B (mounting unit 52B) according to the modification example illustrated in FIG. 6, three projecting portions 527B may be provided by cutting out parts of the projecting portion 527A such that the projecting portion 527A is not continuous on the first virtual circle VC1.

Here, the projecting portions 527B are each positioned at rotationally symmetrical positions at intervals of 120° around the central axis Ax2, on the first virtual circle VC1.

Third Embodiment

Next, a third embodiment will be described.

In the following description, the same reference signs are assigned to the same configurations as those in the first embodiment described above, and thus detailed description thereof is omitted or simplified.

Figure 7:
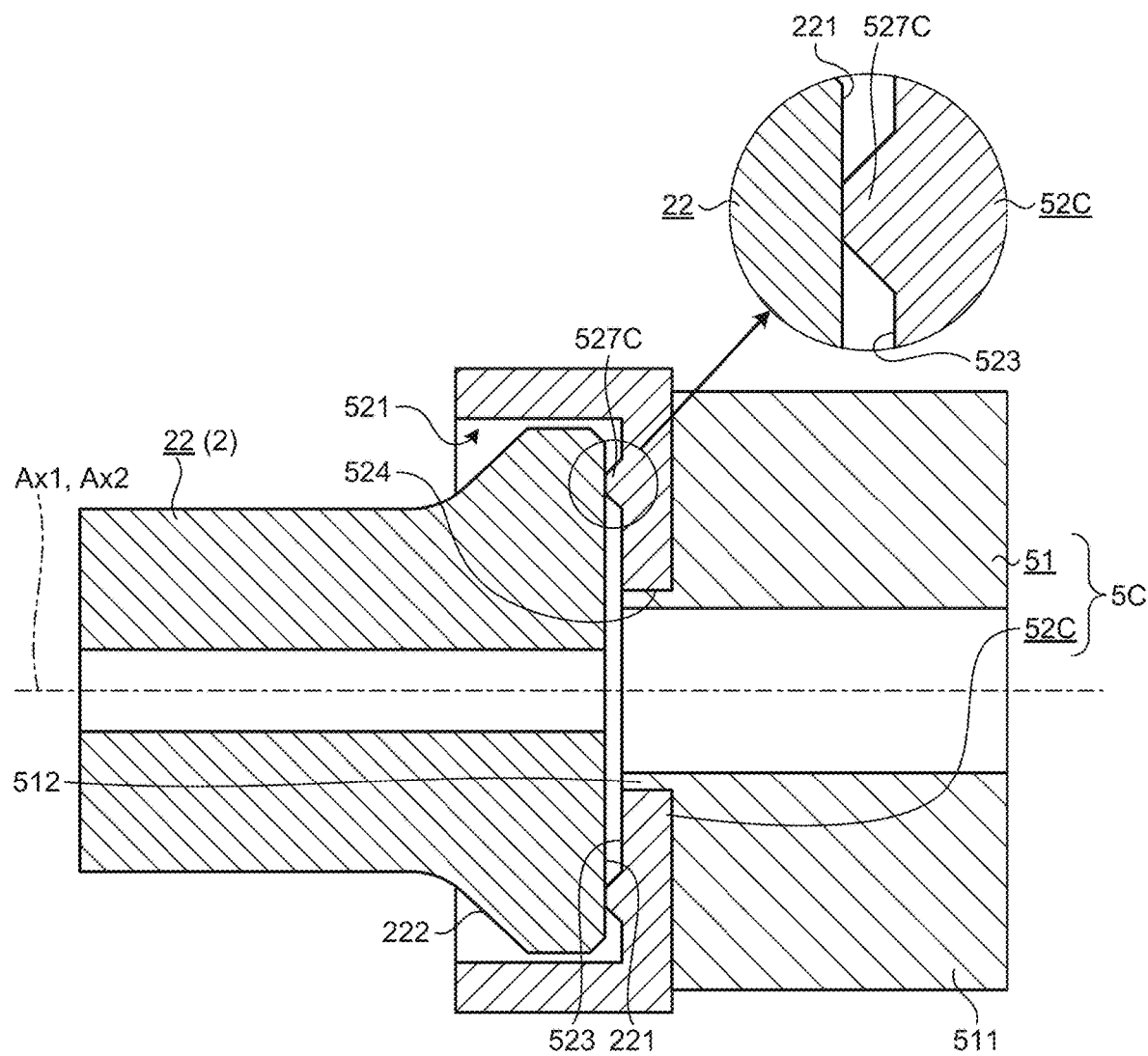
FIG. 7 is a view illustrating a configuration of a mounting unit according to a third embodiment.
Figure 8:
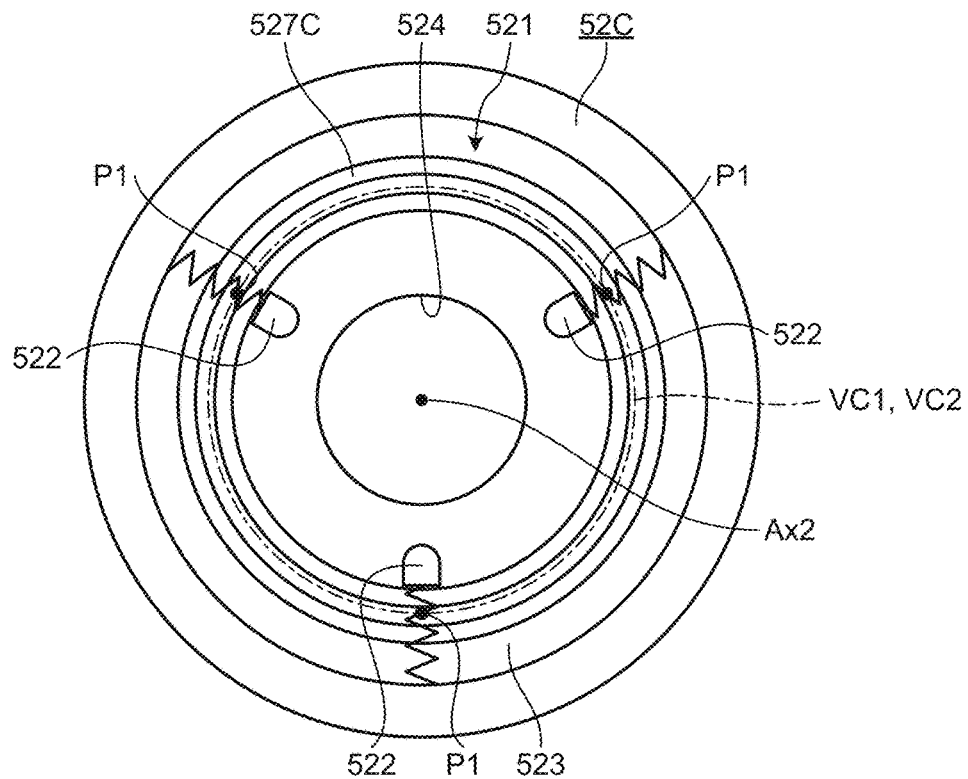
FIG. 8 is a view of the mounting unit viewed from a side on which an eyepiece unit is mounted.

FIG. 7 is a cross-sectional view corresponding to FIG. 2, the view illustrating a configuration of a mounting unit 52C according to the third embodiment. FIG. 8 is a view of the mounting unit 52C viewed from the side on which the eyepiece unit 22 is mounted.

In a camera head 5C (mounting unit 52C) according to the third embodiment, as illustrated in FIG. 7 or 8, there is employed a projecting portion 527C having a different configuration from that of the projecting portion 527 in the camera head 5 (mounting unit 52) described in the first embodiment described above.

Incidentally, in the mounting unit 52C according to the third embodiment, the projecting portion 527C having the different configuration from that of the projecting portions 527 is employed, and thus the attachment hole 525 (including drop preventing protrusion 526) is not provided.

As illustrated in FIG. 7 or 8, the projecting portion 527C is integrally formed on the facing surface 523. The projecting portion 527C projects toward the abutting surface 221 and has an annular shape extending over the entire circumference in the circumferential direction around the central axis Ax2. In addition, in a case of being cut by a plane including the axis Ax2, as illustrated in FIG. 7, a projecting end of the projecting portion 527C has a flat surface orthogonal to the central axis Ax2. In this manner, in a state in which the eyepiece unit 22 is mounted on the mounting unit 52C, the projecting portion 527C abuts the abutting surface 221 by the flat surface.

Incidentally, the projecting end (flat surface) of the projecting portion 527C configures the first virtual circle VC1 described in the first embodiment described above and matches the second virtual circle VC2, when viewed from the direction along the central axis Ax2.

Even in a case of employing the projecting portion 527C as described in the third embodiment described above, the same effects as those of the first embodiment are achieved.

Modification Example of Third Embodiment

Figure 9:
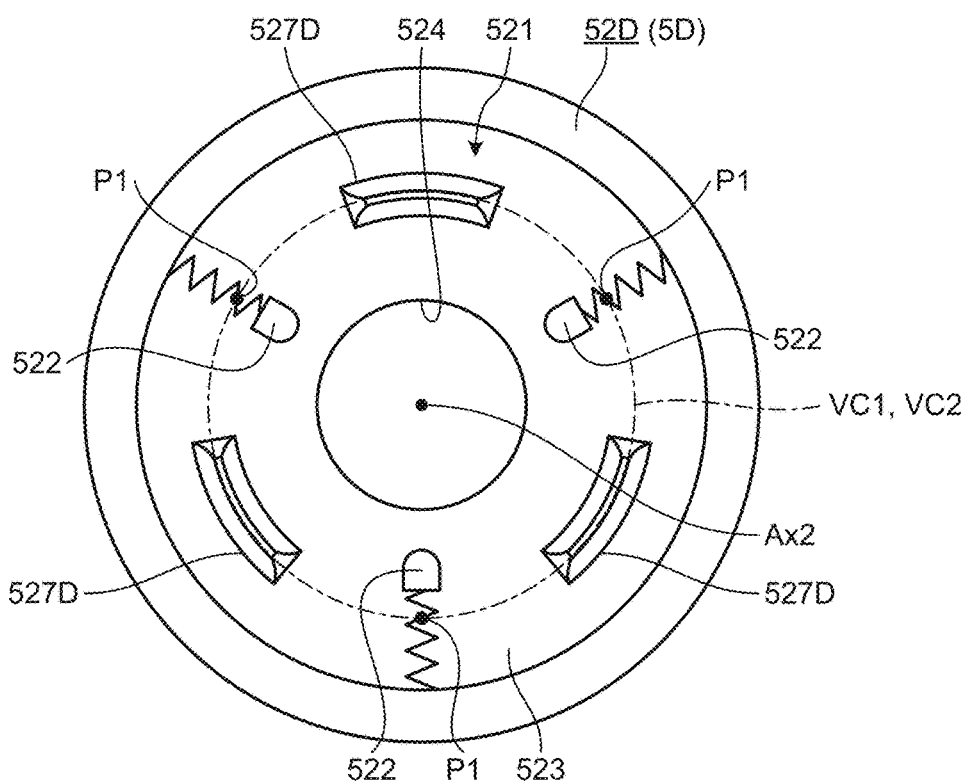
FIG. 9 is a view illustrating a modification example of the third embodiment.

FIG. 9 is a view corresponding to FIG. 8, the view illustrating a modification example of the third embodiment.

In the third embodiment described above, the projecting portion 527C has the annular shape extending over the entire circumference in the circumferential direction around the central axis Ax2; however, the shape of the projecting portion is not limited thereto.

For example, as illustrated in a camera head 5D (mounting unit 52D) according to the modification example illustrated in FIG. 9, three projecting portions 527D may be provided by cutting out parts of the projecting portion 527C such that the projecting portion 527C is not continuous on the first virtual circle VC1.

Here, the projecting portions 527D are each positioned at rotationally symmetrical positions at intervals of 120° around the central axis Ax2, on the first virtual circle VC1.

Fourth Embodiment

Next, a fourth embodiment will be described.

In the following description, the same reference signs are assigned to the same configurations as those in the first and third embodiments described above, and thus detailed description thereof is omitted or simplified.

Figure 10B:
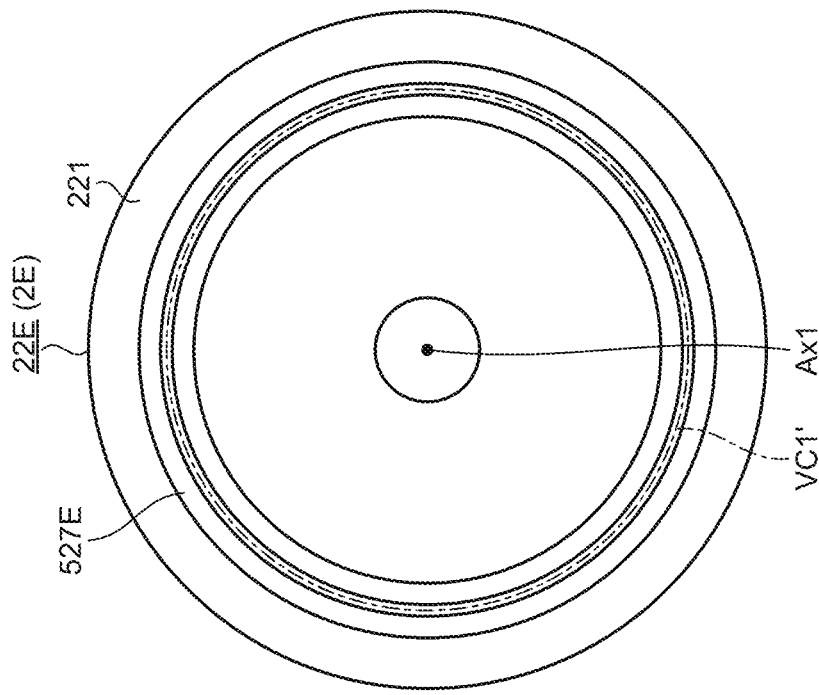
FIGS. 10A and 10B are views illustrating a configuration of an eyepiece unit according to a fourth embodiment.
Figure 10A:
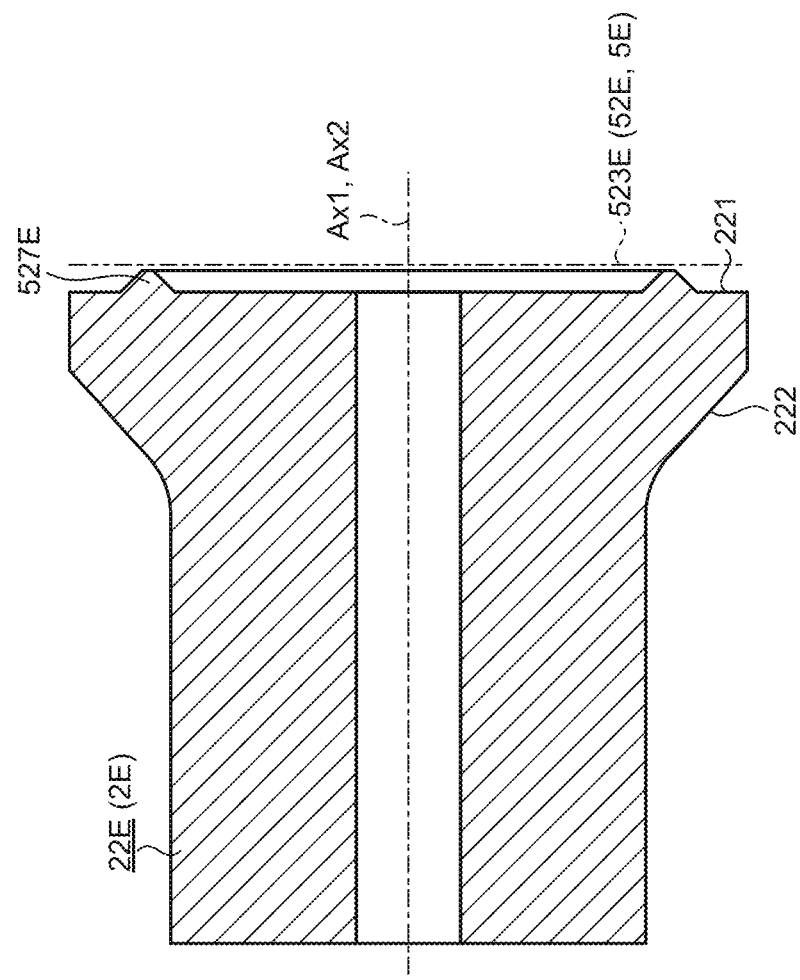

FIGS. 10A and 10B are views illustrating a configuration of an eyepiece unit 22E according to the fourth embodiment. Specifically, FIG. 10A is a cross-sectional view corresponding to FIGS. 2 and 7. FIG. 10B is a view of the eyepiece unit 22E when viewed from the proximal end side (side of a right end portion in FIG. 10A).

In the fourth embodiment, as illustrated in FIGS. 10A and 10B, the position at which the projecting portion 527C is provided in the third embodiment described above is changed to the abutting surface 221 and is not provided on the facing surface 523.

Specifically, in an endoscope 2E (eyepiece unit 22E) according to the fourth embodiment, a projecting portion 527E (FIGS. 10A and 10B) having the same shape as that of the projecting portion 527C is integrally formed on the abutting surface 221.

Here, a projecting end (flat surface) of the projecting portion 527E configures a first virtual circle VC1' (FIG. 10B) around the central axis Ax1 and matches the second virtual circle VC2, when viewed from the direction along the central axis Ax1.

On the other hand, in a camera head 5E (mounting unit 52E) according to the fourth embodiment, a facing surface 523E does not provided with the projecting portion 527C, unlike the facing surface 523 described in the third embodiment described above. Incidentally, in FIG. 10A, for convenience of description, only the facing surface 523E is represented by a dot-and-dash line as the camera head 5E. In addition, the facing surface 523E is orthogonal to the central axis Ax2 and extends over the entire circumference in the circumferential direction around the central axis Ax2.

In this manner, in a state in which the eyepiece unit 22E is mounted on the mounting unit 52E, the projecting end (flat surface) of the projecting portion 527E abuts the facing surface 523E.

Even in a case of employing the projecting portion 527E in the endoscope 2E as described in the fourth embodiment described above, the same effects as those of the first and third embodiments are achieved.

Modification Example of Fourth Embodiment

Figure 11B:
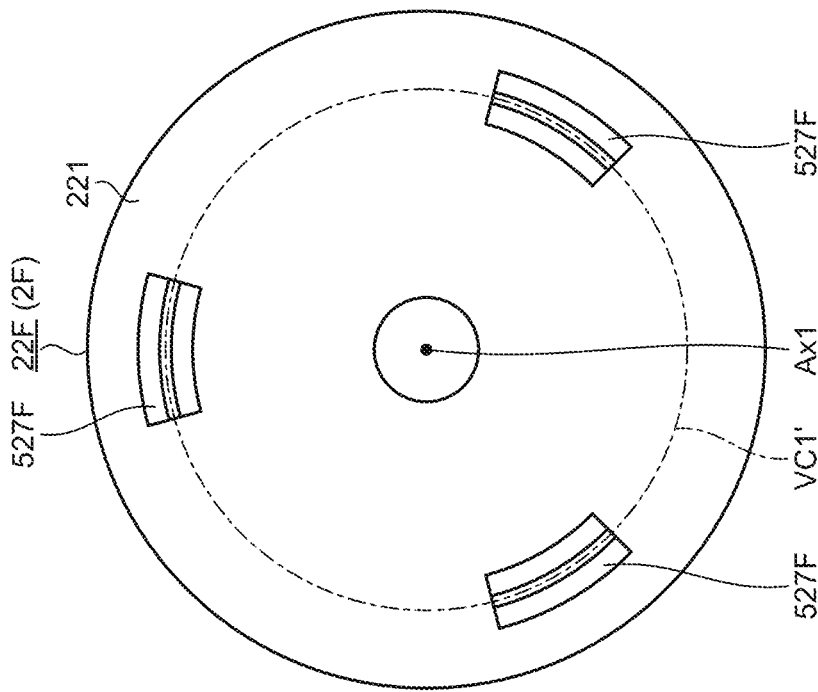
FIGS. 11A and 11B are views illustrating a modification example of the fourth embodiment.
Figure 11A:
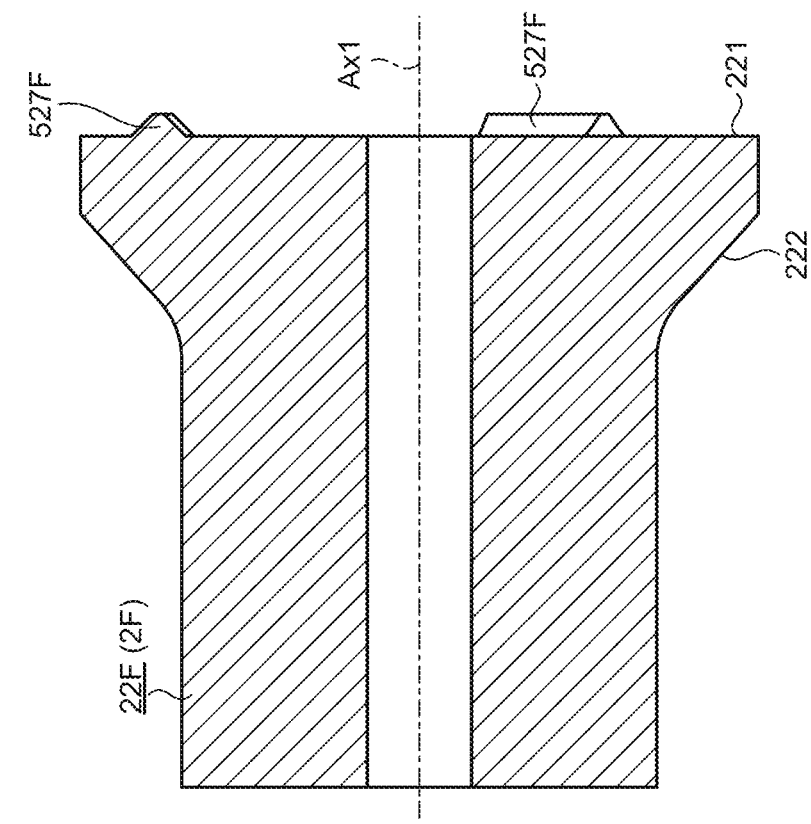

FIGS. 11A and 11B are views corresponding to FIGS. 10A and 10B, the views illustrating a modification example of the fourth embodiment.

In the fourth embodiment described above, the projecting portion 527E has the annular shape extending over the entire circumference in the circumferential direction around the central axis Ax1; however, the shape of the projecting portion is not limited thereto.

For example, as illustrated in an endoscope 2F (eyepiece unit 22F) according to the modification example illustrated in FIGS. 11A and 11B, three projecting portions 527F may be provided by cutting out parts of the projecting portion 527E such that the projecting portion 527E is not continuous on the first virtual circle VC1'.

Here, the projecting portions 527F are each positioned at rotationally symmetrical positions at intervals of 120° around the central axis Ax1, on the first virtual circle VC1'.

Fifth Embodiment

Next, a fifth embodiment will be described.

In the following description, the same reference signs are assigned to the same configurations as those in the first, second, and fourth embodiments described above, and thus detailed description thereof is omitted or simplified.

Figure 12B:
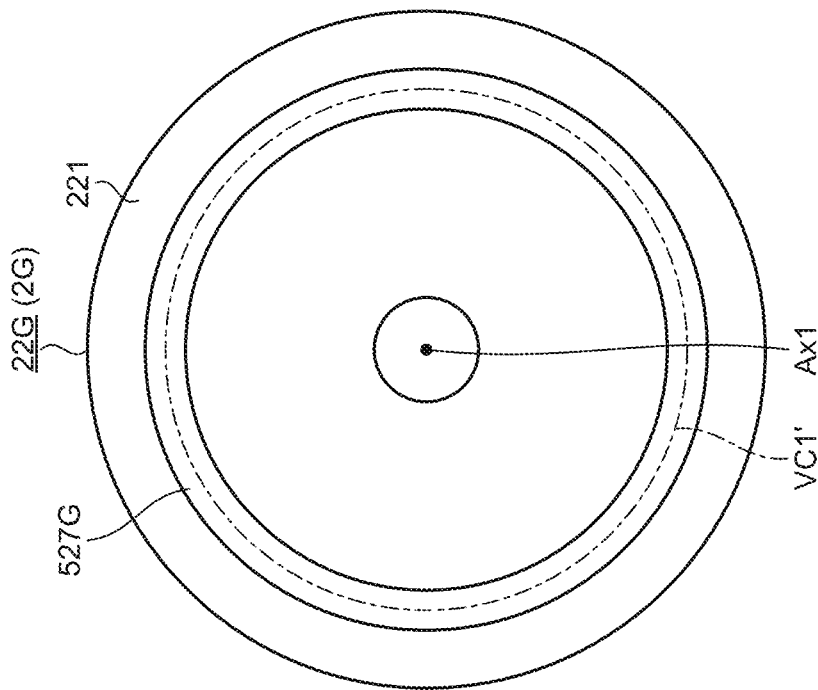
FIGS. 12A and 12B are views illustrating a configuration of an eyepiece unit according to a fifth embodiment.
Figure 12A:
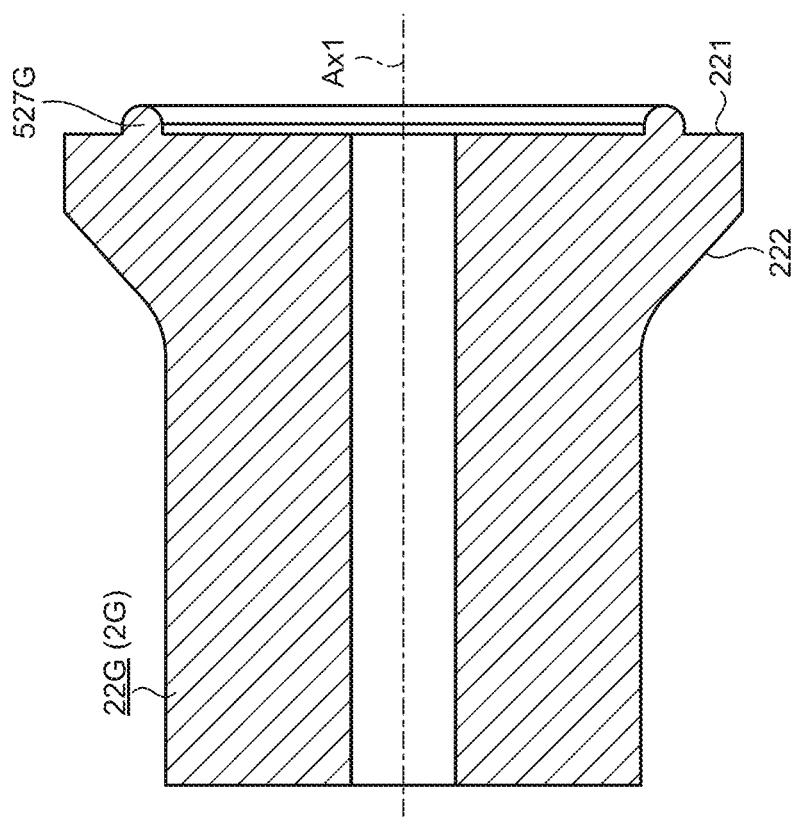

FIGS. 12A and 12B are views corresponding to FIGS. 11A and 11B, the views illustrating a configuration of an eyepiece unit 22G according to the fifth embodiment.

In the fifth embodiment, as illustrated in FIGS. 12A and 12B, the position at which the projecting portion 527A is provided in the second embodiment described above is changed to the abutting surface 221 and is not provided on the facing surface 523.

Specifically, in an endoscope 2G (eyepiece unit 22G) according to the fifth embodiment, a projecting portion 527G (FIGS. 12A and 12B) having the same shape as that of the projecting portion 527A is integrally formed on the abutting surface 221.

Here, a projecting end of the projecting portion 527G configures the first virtual circle VC1' (FIG. 12B) around the central axis Ax1 and matches the second virtual circle VC2, when viewed from the direction along the central axis Ax1.

Incidentally, the camera head according to the fifth embodiment is not specifically described in the drawing; however, the camera head 5E described in the fourth embodiment described above is employed.

In this manner, in a state in which the eyepiece unit 22G is mounted on the mounting unit 52E, the projecting end of the projecting portion 527G abuts the facing surface 523E.

Even in a case of employing the projecting portion 527G in the endoscope 2G as described in the fifth embodiment described above, the same effects as those of the first and second embodiments are achieved.

Modification Example of Fifth Embodiment

Figure 13B:
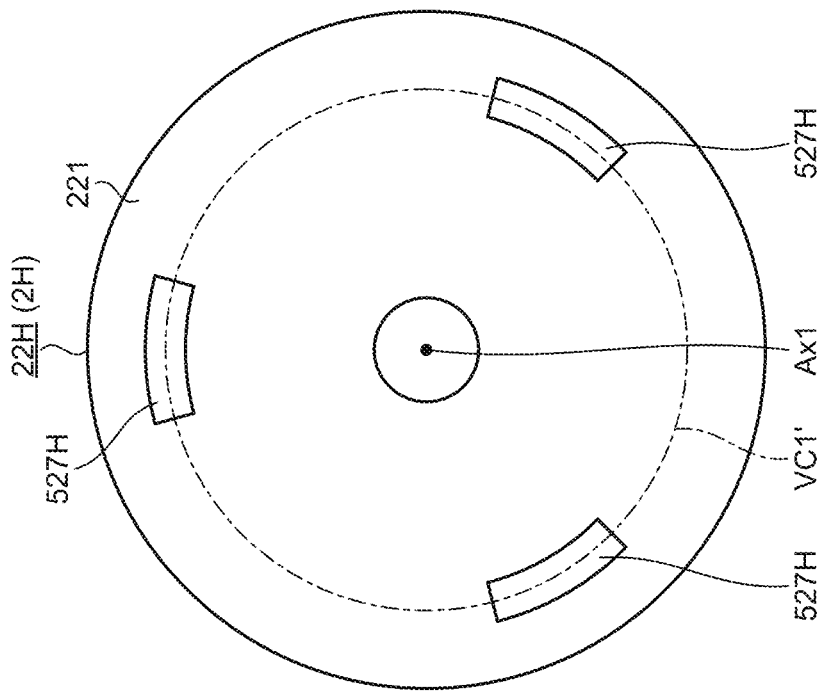
FIGS. 13A and 13B are views illustrating a modification example of the fifth embodiment.
Figure 13A:
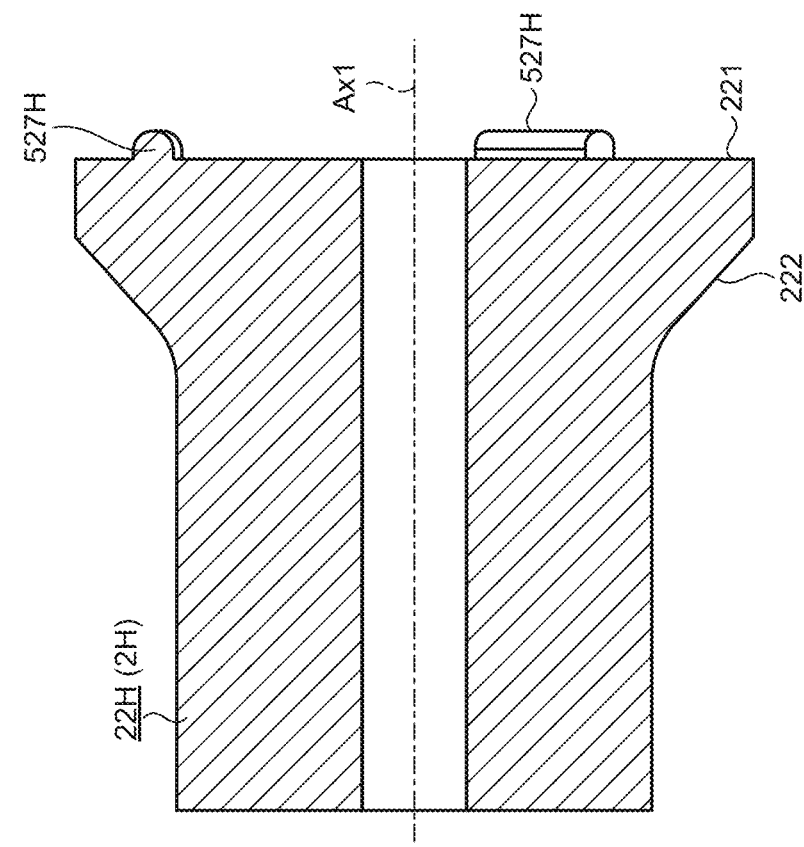

FIGS. 13A and 13B are views corresponding to FIGS. 12A and 12B, the views illustrating a modification example of the fifth embodiment.

In the fifth embodiment described above, the projecting portion 527G has the annular shape extending over the entire circumference in the circumferential direction around the central axis Ax1; however, the shape of the projecting portion is not limited thereto.

For example, as illustrated in an endoscope 2H (eyepiece unit 22H) according to the modification example illustrated in FIGS. 13A and 13B, three projecting portions 527H may be provided by cutting out parts of the projecting portion 527G such that the projecting portion 527G is not continuous on the first virtual circle VC1'.

Here, the projecting portions 527H are each positioned at rotationally symmetrical positions at intervals of 120°, around the central axis Ax1, on the first virtual circle VC1'.

Sixth Embodiment

Next, a sixth embodiment will be described.

In the following description, the same reference signs are assigned to the same configurations as those in the first and fourth embodiments described above, and thus detailed description thereof is omitted or simplified.

Figure 14B:
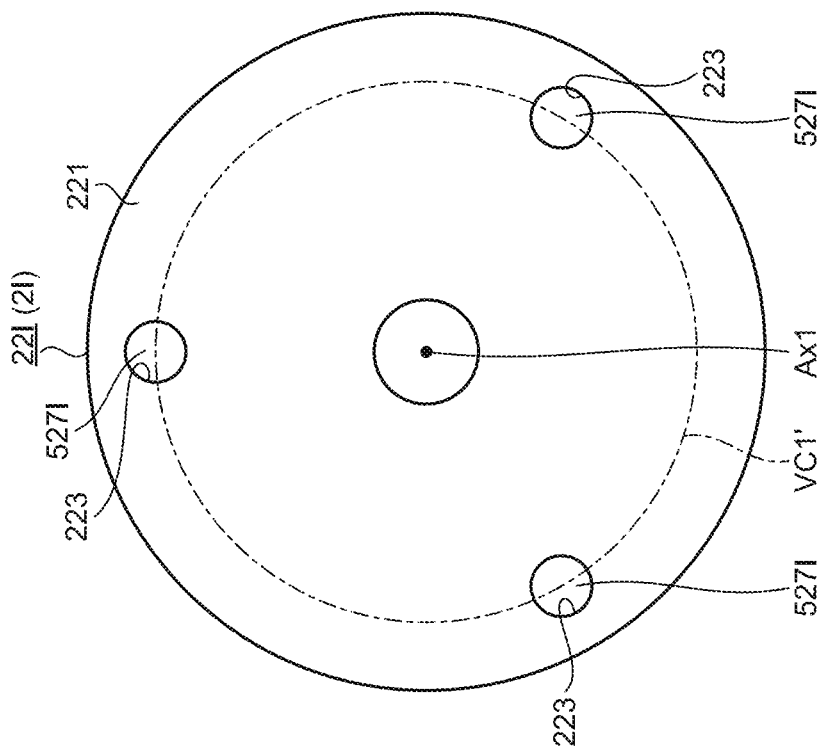
FIGS. 14A and 14B are views illustrating a configuration of an eyepiece unit according to a sixth embodiment.
Figure 14A:
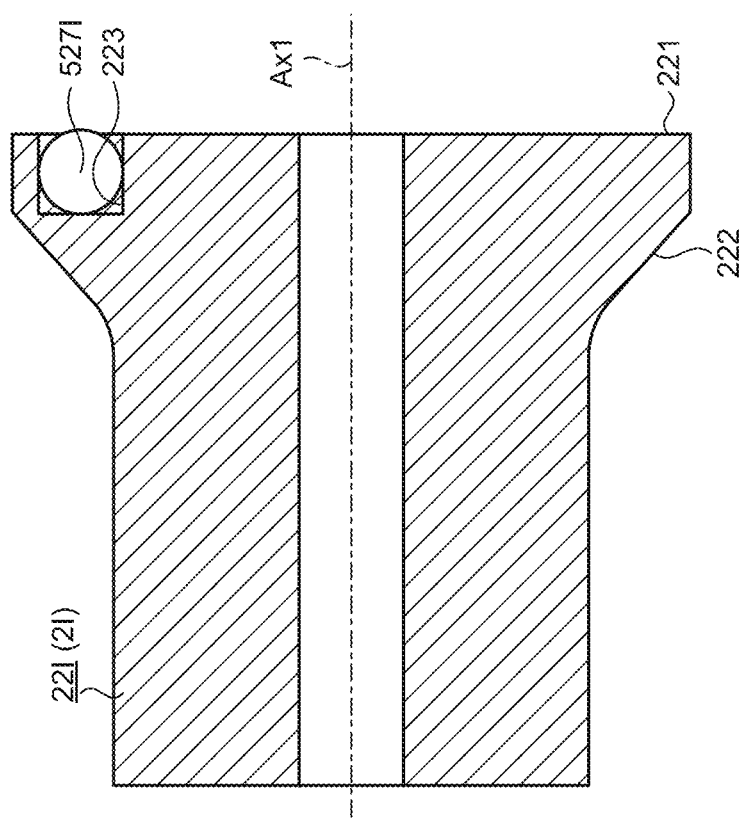

FIGS. 14A and 14B are views corresponding to FIGS. 11A and 11B, the views illustrating a configuration of an eyepiece unit 22I according to the sixth embodiment.

In the sixth embodiment, as illustrated in FIGS. 14A and 14B, the position at which the projecting portion 527 is provided in the first embodiment described above is changed to the eyepiece unit 22 instead of the mounting unit 52.

Incidentally, the camera head according to the sixth embodiment is not specifically described in the drawing; however, the camera head 5E described in the fourth embodiment described above is employed.

Specifically, in an endoscope 2I (eyepiece unit 22I) according to the sixth embodiment, the abutting surface 221 is provided with an attaching recessed portion 223.

The attaching recessed portion 223 has a circular shape in plan view when viewed from a direction along the central axis Ax1. As illustrated in FIG. 14B, three attaching recessed portions 223 are provided and have the same shape as each other. In addition, the attaching recessed portions 223 are each provided at rotationally symmetrical positions at intervals of 120° around the central axis Ax1 on the first virtual circle VC1' around the central axis Ax1. Incidentally, the first virtual circle VC1' matches the second virtual circle VC2, when viewed from a direction along the central axis Ax1. In this manner, as illustrated in FIGS. 14A and 14B, a projecting portion 527I is housed inside the attaching recessed portion 223.

Three projecting portions 527I are each configured of a ball (spherical body) having the same shape as that of the projecting portion 527 described in the first embodiment described above. In this manner, in a state in which the projecting portions 527I are housed in the attaching recessed portions 223, a part of each of the projecting portions projects from the abutting surface 221 toward the facing surface 523E and is rotatably attached to the eyepiece unit 22I. In addition, in a state in which the eyepiece unit 22E is mounted on the mounting unit 52E, the projecting portions 527I abut the facing surface 523E.

Even in a case of employing the projecting portion 527I in the endoscope 2I as described in the sixth embodiment described above, the same effects as those of the first embodiment are achieved.

Other Embodiments

As described above, the modes for carrying out the disclosure are described; however, the disclosure is not limited to the first to sixth embodiments and the modification examples thereof described above.

In the first to sixth embodiments and the modification examples thereof described above, at least three projecting portions 527 and 527A to 527G and at least three pressing portions 522 may be provided, and four or more projecting portions and four or more pressing portions may be provided, for example. In addition, the number of the projecting portions 527 and 527A to 527G and the number of the pressing portion 522 may be the same as each other or different from each other.

In the first to sixth embodiments and the modification examples thereof described above, there may be employed a configuration in which the first virtual circles VC1 and VC1' are positioned on an outer side of the second virtual circle VC2 when viewed from the direction along the central axis Ax1 (Ax2).

In the first embodiment described above and the modification examples of the second and third embodiments described above, the angle θ in the rotation direction between the adjacent projecting portions 527, 527B, or 527D and the pressing positions P1 by the adjacent pressing portions 522 in the rotation direction around the central axis Ax2 may be set to 0°.

In the first to sixth embodiments and the modification examples thereof described above, the endoscope 2 and 2E to 2I are not limited to the rigid endoscope and may be a flexible endoscope.

In the first to sixth embodiments and the modification examples thereof described above, a use of the endoscope apparatus 1 may not be limited to the medical field, and the endoscope apparatus may be used in the industrial field and may be an endoscope apparatus for observing the inside of the subject such as a mechanical structure.

A camera head and an endoscope according to the disclosure achieve an effect that it is possible to improve operability.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head comprising a mount which is detachably connected to an eyepiece of an endoscope, the eyepiece includes an abutting surface that is orthogonal to a central axis of the endoscope, the central axis being along an insertion direction of the endoscope into a subject, the camera head capturing an object image emitted from the eyepiece, wherein
the mount is to be connected to the eyepiece to relatively rotate the endoscope and the camer head around the central axis,
the mount includes
a facing surface that faces the abutting surface, and
a pusher that abuts the eyepiece and presses the eyepiece toward the facing surface along the central axis while allowing the endoscope and the camera head to relatively rotate around the central axis, and
the facing surface includes a projection that projects toward the abutting surface and abuts the abutting surface.

2. The camera head according to claim 1, wherein the projection has an ar nular shape extending over the entire circumference in the circumferential direction around the central axis.

3. The camera head according to claim 1, wherein the facing surface includes at least three of the projections.

4. The camera head according to claim 3, wherein the projections are each provided at rotationally symmetrical positions around the central axis.

5. The camera head according to claim 3, wherein each of the projections is a ball of which a part projects from the facing surface toward the abutting surface and is rotatably attached to the mount.

6. The camera head according to claim 1, wherein the projections have a curved surface that has an arc shape in cross-sectional view and abuts the abutting surface.

7. The camera head according to claim 1, wherein the projections have a flat surface that abuts the abutting surface.

8. The camera head according to claim 1, wherein the mount includes at least three of the pushers.

9. The camera head according to claim 8, wherein the pushers are provided at rotationally symmetrical positions around the central axis.

10. The camera head according to claim 8, wherein
the projections are provided at at least three positions on a first virtual circle around the central axis,
the eyepiece is provided with an inclined surface that is separated from the central axis toward a side of the facing surface,
the pushers each abut the inclined surface and each press the eyepiece toward the facing surface along the central axis,
abutting positions between the pushers and the inclined surface are each positioned on a second virtual circle around the central axis, and
the first virtual circle is positioned at a position matching the second virtual circle or on an outer side from the second virtual circle when viewed from a direction along the central axis.

11. The camera head according to claim 8, wherein
the projections are provided on the first virtual circle around the central axis by same number as that of the pushers and each are provided at rotationally symmetrical positions around the central axis,
the eyepiece is provided with the inclined surface that is separated from the central axis toward the side of the facing surface,
the pushers each abut the inclined surface and each press the eyepiece toward the facing surface along the central axis, and
abutting positions between the pushers and the inclined surface are each positioned at positions identical to positions of the projections in a rotation direction around the central axis when viewed from a direction along the central axis or at positions at which angles in the rotation direction between adjacent projections in the rotation direction are identical to each other.

12. The camera head according to claim 1, wherein the projection extends further along a circumferential direction than a radial direction.

13. An endoscope comprising an eyepiece which is detachably connected to a mount of a camera head, the endoscope taking an object image of an inside of a subject and emitting the image from the eyepiece, wherein the mount includes a facing surface that is orthogonal to a central axis of the endoscope, the central axis being along an insertion direction of the endoscope into the subject, and the facing surface extending over an entire circumference in a circumferential direction around the central axis, and a pusher that abuts the eyepiece and presses the eyepiece toward the facing surface along the central axis while allowing the endoscope and the camera head to relatively rotate around the central axis, wherein
the eyepiece is to be connected to the mount to relatively rotate the endoscope and the camera head around the central axis,
the eyepiece includes an abutting surface that faces the facing surface, and
the abutting surface includes a projection that projects toward the facing surface and abuts the facing surface.

14. The endoscope according to claim 13, wherein the projection extends further along a circumferential direction than a radial direction.

15. The endoscope according to claim 13, wherein the projection has an annular shape extending over the entire circumference in the circumferential direction around the central axis.

16. The endoscope according to claim 13, wherein the facing surface includes at least three of the projections.

17. The endoscope according to claim 16, wherein the projections are each provided at rotationally symmetrical positions around the central axis.

18. The endoscope according to claim 16, wherein each of the projections is a ball of which a part projects from the facing surface toward the abutting surface and is rotatably attached to the mount.

19. The endoscope according to claim 13, wherein the projections have a curved surface that has an arc shape in cross-sectional view and abuts the abutting surface.

20. The endoscope according to claim 13, wherein the projections have a flat surface that abuts the abutting surface.

* * * * *